United States Patent
Baerthele et al.

(10) Patent No.: US 10,172,510 B2
(45) Date of Patent: Jan. 8, 2019

(54) MICROINVASIVE MEDICAL INSTRUMENT (71) Applicant: KARL STORZ GmbH & Co. KG, Tuttlingen (DE)

(72) Inventors: Andreas Baerthele, Reichenau (DE); Michael Egle, Boettingen (DE); Uwe Wittke, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 203 days.

(21) Appl. No.: 15/248,340

(22) Filed: Aug. 26, 2016

(65) Prior Publication Data
US 2017/0055812 A1 Mar. 2, 2017

(30) Foreign Application Priority Data
Aug. 27, 2015 (DE) ......................... 10 2015 114 264

(51) Int. Cl.
| | | |
|---|---|---|
| *A61B 1/00* | (2006.01) | |
| *A61B 1/303* | (2006.01) | |
| *A61B 17/42* | (2006.01) | |
| *A61B 1/04* | (2006.01) | |
| *A61B 17/00* | (2006.01) | |
| *A61B 17/34* | (2006.01) | |

(52) U.S. Cl.
CPC ........ *A61B 1/00147* (2013.01); *A61B 1/0014* (2013.01); *A61B 1/00135* (2013.01); *A61B 1/303* (2013.01); *A61B 17/3421* (2013.01); *A61B 17/42* (2013.01); *A61B 1/00128* (2013.01); *A61B 2017/00367* (2013.01); *A61B 2017/347* (2013.01)

(58) Field of Classification Search
CPC . A61B 1/00147; A61B 1/303; A61B 1/00135; A61B 1/00154; A61B 1/00142; A61B 1/0014; A61B 1/00128; A61B 1/005; A61B 17/42; A61B 17/3421; A61B 2017/00367; A61B 2017/347
See application file for complete search history.

(56) References Cited

U.S. PATENT DOCUMENTS

| | | | |
|---|---|---|---|
| 5,624,431 A | | 4/1997 | Gerry et al. |
| 5,797,836 A | * | 8/1998 | Lucey ................ A61B 1/00179 |
| | | | 600/109 |

FOREIGN PATENT DOCUMENTS

| | | |
|---|---|---|
| DE | 42 11 417 A1 | 10/1993 |
| DE | 195 05 032 A1 | 8/1995 |

(Continued)

*Primary Examiner* — Timothy J Neal
(74) *Attorney, Agent, or Firm* — Muncy, Geissler, Olds & Lowe, P.C.

(57) ABSTRACT

A medical instrument (10) comprises an effecting device (40), which is movable in a first direction (48) from a first effecting position into a second effecting position, a pushbutton (60), which is movable manually in a second direction (68) from a first button position into a second button position, and a lever (70), which is pivotable about a pivot axis (78). The lever (70) mechanically couples the pushbutton (60) and the effecting device (40) in such a way that a movement of the pushbutton (60) in the second direction (68) is accompanied by a movement of the effecting device (40) in the first direction (48), which is opposite to the second direction (68). The lever (70) does not have an area that is rotationally symmetrical to the pivot axis (78) in the region of the pivot axis (78).

13 Claims, 6 Drawing Sheets (56) References Cited

FOREIGN PATENT DOCUMENTS

| DE | 692 12 259 T2 | 12/1996 |
| DE | 10 2008 024 900 A1 | 12/2009 |
| EP | 0 157 888 A1 | 10/1985 |
| EP | 1 952 769 B1 | 4/2014 |
| WO | WO 2007/106813 A2 | 9/2007 |
| WO | WO 2014/145595 A2 | 9/2014 |

* cited by examiner

MICROINVASIVE MEDICAL INSTRUMENT

This nonprovisional application claims priority under 35 U.S.C. § 119(a) to German Patent Application No. 10 2015 114 264.3, which was filed in Germany on Aug. 27, 2015, and which is herein incorporated by reference.

BACKGROUND OF THE INVENTION

Field of the Invention

The present invention is based on a microinvasive or other medical instrument, in particular a hysteroscope or some other medical instrument, in which a first component part is displaceable in relation to a second component part or is in some other way movable and can be arrested in at least one position. The invention is based in particular on such a medical instrument in which the arrestment by an arresting slide, which engages in a clearance, can be released by manual pressure on a pushbutton.

Description of the Background Art

Medical instruments for microinvasive or other applications must simultaneously satisfy numerous requirements, some of which are difficult to reconcile with one another. They must be robust, i.e. act reliably and precisely even after mechanically rough treatment by medical personnel. Particularly microinvasive medical instruments or medical instruments for microinvasive applications must also generally have smallest possible dimensions and cross sections. They are intended to be simple to handle and operate, and it is intended that this can be easily learned and is possible as intuitively as possible. In addition to this, it is required that they can be disassembled as extensively as possible as simply and quickly as possible, to allow them to be cleaned as completely as possible after use.

Constructions that are known from other areas of technology often cannot be used under these conditions, or at best in a greatly modified form.

SUMMARY OF THE INVENTION

One object of the present invention is to provide an improved medical instrument, in particular an improved microinvasive medical instrument.

This object is achieved by the subjects of the independent claims.

Developments are specified in the dependent claims.

Embodiments of the present invention are based on the idea that, in a medical instrument, a rocker or a lever for transmitting a movement in a first direction into a movement in an opposite second direction is not to be conventionally mounted by means of a shaft or one or more journals or a combination of a recess and a ridge or a flexure, but instead that the resultant mobility of the lever in its longitudinal direction is to be accepted or prevented in some other way.

A medical instrument comprises an effecting device, which is movable in a first direction from a first effecting position into a second effecting position, a pushbutton, which is movable manually in a second direction from a first button position into a second button position, and a lever, which is pivotable about a pivot axis, the second direction being different from the first direction, the lever mechanically coupling the pushbutton and the effecting device in such a way that a movement of the pushbutton in the second direction is accompanied by a movement of the effecting device in the first direction, and the lever not having an area that is rotationally symmetrical to its pivot axis in the region of the pivot axis.

The medical instrument is in particular a microinvasive medical instrument or a medical instrument for use when performing microinvasive measures. The effecting device is guided in particular in such a way that it can be moved only or substantial only (i.e. apart from play) in the first direction or opposite thereto. The pushbutton is guided in particular in such a way that it can be moved only or substantially only (i.e. apart from play) in the second direction or opposite thereto. The pivot axis about which the lever is pivotable is in particular orthogonal to the first direction and the second direction. The second direction is in particular opposite to the first direction.

In the region of the pivot axis, the lever is in particular simply bar-shaped or rod-shaped or has a cylindrical form with a circular, rectangular or other cross section and a cylinder axis orthogonal to the pivot axis. In particular, the entire lever is cylindrical or substantially cylindrical with an axis of symmetry orthogonal to the pivot axis of the lever.

In particular, the lever does not have a shaft, a journal or a bore for receiving a shaft. In particular, the lever also does not have a recess and a ridge for mounting.

Dispensing with a shaft, a journal, a recess, a ridge or a bore on the lever for the definition of the pivot axis allows production of the lever to be significantly simplified and more extensive miniaturization to be made possible. Furthermore, dispensing with a shaft, a bore, a journal, a recess and a ridge allows the assembly of the medical instrument to be simplified. In particular, the lever may be designed such that a specific orientation of the lever (in the sense of a rotation about its longitudinal axis) is not required when it is inserted into the medical instrument.

The displaceability of the lever that results from the absence of a conventional bearing can be disregarded, in particular in the case where the medical instrument is designed in such a way that the lever is pivoted only by small angles during the intended use. Alternatively, and in particular in the case where the medical instrument is designed in such a way that pivoting of the lever not only by small angles is intended, measures described below can ensure the intended arrangement of the lever.

In the case of a medical instrument such as that described here, a middle region of the lever protrudes in particular through an opening in a wall between the pushbutton and the effecting device, the middle region of the lever being mechanically guided through the opening in the wall such that the lever is pivotable about the pivot axis, but is not displaceable, or not significantly, in the first direction or the second direction.

The lever is not significantly displaceable in the first direction if the distance over which the lever is displaceable parallel to the first direction is small in relation to the paths that the ends of the lever cover between the intended extreme angular positions of the lever, that is to say is for example only half, a third, a fifth or a tenth. The lever and the opening are in particular designed in such a way that, in one or both intended extreme angular positions of the lever, they simultaneously abut on two regions of the periphery of the opening that lie opposite one another in the first direction and/or in the second direction. As a result, the transmission ratio imparted by the lever between the pushbutton and the effecting device can be exactly defined, at least with respect to the entire intended pivoting range of the lever.

In the case of a medical instrument such as that described here, the wall has in particular a reduced thickness in the vicinity of the opening.

In the vicinity of the opening, the thickness of the wall may be reduced for example by a conical bore or by a cylindrical bore, which does not penetrate the wall completely or only in the region of the opening. The thickness of the wall is reduced in the vicinity of the opening for example to at most half, at most a third, at most a fifth or at most a tenth.

A thickness of the wall that is reduced in the region of the opening allows a greater pivoting range of the lever and/or improved guidance of the lever even between its extreme angular positions to be achieved.

In the case of a medical instrument such as that described here, the lever has in particular a first end, which engages in a clearance in the effecting device, and a second end, which engages in a clearance in the pushbutton.

The first end of the lever and the clearance in the effecting device are designed in particular in such a way that the first end of the lever is guided in the clearance in the effecting device with little friction, and especially with little play. The second end of the lever and the clearance in the pushbutton are designed in particular in such a way that the second end of the lever is guided in the clearance in the pushbutton with little friction, and especially with little play.

The clearance in the effecting device is formed for example by a blind bore or a through-bore that is closed on one side. The clearance in the pushbutton is formed for example by a blind bore or a through-bore that is closed on one side. In particular, at least one of the two clearances is formed by a through-bore that has been closed on one side after the insertion of the lever.

If both the clearance in the effecting device and the clearance in the pushbutton respectively have only one opening, that is to say for example do not have the form of through-bores but of blind bores, the clearance in the effecting device and the clearance in the pushbutton can be designed such that the lever is at all times retained substantially in its intended position. In particular, in this case the lever cannot be removed from its intended position, or not just by a movement in the direction parallel to its longitudinal direction or longitudinal axis.

A medical instrument such as that described here also comprises in particular an O-ring of an elastic material, either the O-ring abutting on the second end of the lever and pushing the first end of the lever into the clearance in the effecting device or the O-ring abutting on the first end of the lever and pushing the second end of the lever into the clearance in the pushbutton.

The O-ring is formed in particular from rubber or natural rubber or synthetic rubber or some other elastomer or some other elastic material.

The fact that the O-ring abuts on one end of the lever and pushes the lever in its longitudinal direction or substantially in its longitudinal direction toward the opposite end means that it can ensure a defined position of the lever. Even when it is of a high quality, an O-ring can be a low-cost component and can significantly simplify the production of the medical instrument, in particular in comparison with mounting of the lever by means of a shaft, one or more journals or a combination of a recess and a ridge.

In the case of a medical instrument such as that described here, the lever is in particular designed such that, within its entire intended pivoting range, both ends of the lever simultaneously abut on surfaces lying opposite one another.

The surfaces that are simultaneously abutted or substantially abutted by the ends of the lever within its entire pivoting range, or a great part of its pivoting range, lying opposite one another and in particular parallel or substantially parallel, are in particular subregions of the inner surfaces of the mentioned clearances in the effecting device and in the pushbutton.

In order to make simultaneous abutment of both ends of the lever possible, the ends of the lever are designed in particular as segments of the surface of a circular cylinder or as segments of surfaces of circular cylinders of which the axes coincide or as segments of the surface of a sphere or as segments of surfaces of spheres of which the center points coincide. A formation of the ends of the lever as segments of the surface of a sphere or of surfaces of two spheres with an identical center point can make satisfactory functioning of the lever possible even with any desired rotation of the lever about its longitudinal axis. The axis or the coinciding axes of the circular cylinders or the center point or the coinciding center points of the spheres may lie in the plane of the mentioned opening in a wall between the pushbutton and the effecting device. Alternatively, the coinciding axes of the circular cylinders or the coinciding center points of the spheres may be arranged outside the mentioned opening in the wall between the pushbutton and the effecting device.

In the case of a medical instrument such as that described here, the effecting device is in particular an arresting slide or is mechanically coupled with an arresting slide, the arresting slide being intended for the interlocking retention of a component part of the mechanical instrument in a predetermined position.

The arresting slide may be designed as a pawl or with an inclined flank, so that it only retains the component part of the medical instrument in the predetermined position against forces in one direction, but not when there is a sufficiently great force in the opposite direction. Alternatively, the arresting slide may be designed to retain the component part of the medical instrument in the predetermined position in two opposite directions. The arresting slide may also be intended for the alternative interlocking retention of the component part of the medical instrument in one or more predetermined positions. The arresting slide is intended in particular for retaining the component part in one or more predetermined positions by interlocking engagement in a clearance.

In the case of a medical instrument such as that described here, the wall surrounds the effecting device in particular annularly, a region of the pushbutton surrounding the wall annularly.

The wall has in particular substantially (i.e. for example apart from the mentioned opening through which the lever protrudes) the form of part of a lateral surface of a circular cylinder or some other cylinder. The pushbutton or a component of the pushbutton has in particular a cup-shaped form, the periphery of the pushbutton surrounding the wall annularly.

In the case of a medical instrument such as that described here, in particular the effecting device, the wall and the pushbutton are arranged coaxially in certain portions.

A coaxial arrangement can make a particularly compact type of construction possible.

In the case of a medical instrument such as that described here, the effecting device is in particular guided through the wall in an interlocking manner, the pushbutton being guided through the wall in an interlocking manner.

The effecting device is guided through the wall in particular with little friction and with little play in such a way that a movement of the effecting device is substantially only possible in the first direction and in the direction opposite thereto. Optionally, the effecting device may additionally be rotatable about the first direction. The rotation of the effecting device about the first direction may however be prevented, in particular by the lever, or be restricted to a small angular range.

The pushbutton is guided through the wall in particular with little friction and with little play in such a way that a movement of the pushbutton is substantially only possible in the second direction and in the direction opposite thereto. Optionally, the pushbutton may additionally be rotatable about the second direction. This rotation of the pushbutton about the second direction is however prevented, in particular by the lever, or restricted to a small angular range.

Interlocking guidance both of the effecting device and of the pushbutton through the wall is possible in particular in a (partially) coaxial arrangement. The interlocking guidance both of the effecting device and of the pushbutton through the wall can make a particularly compact formation possible.

In the case of a medical instrument such as that described here, the pushbutton comprises in particular a cup-shaped component and an annular component inserted in a cavity of the cup-shaped component, the clearance in the pushbutton being formed in the annular component.

The cup-shaped component has a periphery, which encloses the open side of the cup-shaped component annularly and in particular is toward the outer shank mentioned below. The annular component is in particular inserted into the cup-shaped component in such a way that a periphery of the annular component is arranged flush or substantially flush with the periphery of the cup-shaped component. The annular component is in particular screwed into the cup-shaped component and/or connected to it by a running-around welded or bonded seam.

The clearance in the pushbutton is formed in particular by a through-bore extending in the radial direction in the annular component, the radially outer end of the through-bore being closed by the wall of the cup-shaped component.

In the case of a medical instrument such as that described here, the annular component has in particular a groove that runs around annularly on its outer circumference and in which the O-ring is placed.

The groove intersects in particular the clearance in the pushbutton.

In the case of a medical instrument such as that described here, the clearance in the pushbutton is formed in particular by a window-shaped opening or a through-bore in the annular component.

If the clearance in the pushbutton is formed by a through-bore in the annular component, the axis of the through-bore lies in particular partially within the groove. For example, the centroid of a cross section of the groove lies on the axis of the through-bore in the annular component.

After the insertion of the lever into the through-bore in the annular component, the opening in the wall and the clearance in the effecting device and the subsequent placement of the O-ring in the groove running around the outside, the cup-shaped component can close both the groove and the through-bore in the annular component. As a result, the cup-shaped component can protect the O-ring from harmful mechanical and other effects and—together with the O-ring—retain the lever at the intended position.

In the case of a medical instrument such as that described here, the through-bore has in particular a cross section that increases in stages or continuously toward the outer side of the annular component.

In particular, the through-bore is at least in certain portions conical. A cross section that increases toward the outer side of the annular component can make guidance of the radially outer end of the lever that has less play in particular in the second direction possible and/or a greater pivoting range of the lever.

In the case of a medical instrument such as that described here, in particular interlocking between the lever and the pushbutton and interlocking between the lever and the opening in the wall prevent the pushbutton from being pulled off from the medical instrument.

The lever can consequently have two functions at the same time, specifically that of transmitting the movement of the pushbutton into the (in particular opposite) movement of the effecting device and that of retaining the pushbutton on the medical instrument. This obviates the need for a further device for retaining the pushbutton on the medical instrument and allows installation space to be saved and the production of the medical instrument to be simplified.

A medical instrument such as that described here also comprises in particular a spring or some other elastic device between the effecting device or the outer shank or a tubular region on the outer shank, forming the wall, on the one hand and the pushbutton on the other hand.

The spring or other elastic device can push the pushbutton into the first button position, from which the pushbutton can be moved manually against the force of the spring or the other elastic device to the second button position. The spring or the other elastic device may push the effecting device into the first effecting position indirectly by way of the lever or by acting directly on the effecting device. In the first effecting position, the effecting device may for example engage in a clearance, in order to retain a component part of the medical instrument in a predetermined position in relation to another component part of the medical instrument.

A medical instrument such as that described here also comprises in particular a device for preventing rotation of the pushbutton in relation to the tubular region on the outer shank or in relation to the effecting device.

The device for preventing rotation comprises in particular a pin or a web on the pushbutton, which engages in a corresponding groove parallel to the second direction on the wall. Alternatively, the device for preventing rotation comprises for example a pin or a web on the wall or some other region of the medical instrument that engages in a groove parallel to the second direction in the pushbutton. In the case of the described structure of the pushbutton comprising a cup-shaped component and an annular component, the device for preventing rotation is in particular partially provided on the annular component.

A medical instrument such as that described here is in particular a hysteroscope with an endoscope and an outer shank, the endoscope being displaceable in relation to the outer shank in an axial direction, the effecting device being an arresting device, and the effecting device being intended and designed to engage in a clearance on the endoscope in the first effecting position, in order in this way to arrest the endoscope in a predetermined position in relation to the outer shank.

The axial direction is the direction parallel to the longitudinal axes of the endoscope and the outer shank. The effecting device is in particular arranged near the proximal end of the outer shank. The effecting device is in particular guided movably in relation to the outer shank exclusively in the first direction, which is in particular orthogonal to the axial direction or to the longitudinal axes of the endoscope and the outer shank, and in the opposite direction.

A method for assembling a medical instrument comprises steps of inserting an effecting device into a tubular region of the medical instrument, introducing the tubular region into an annular component, introducing a lever into a clearance in the annular component, into an opening in the tubular region and into a clearance in the effecting device and inserting the annular component into a cup-shaped component.

The tubular region of the medical instrument is in particular provided on an outer shank of the medical instrument and arranged orthogonally or substantially orthogonally to the longitudinal axis of the outer shank. The insertion of the annular component into the cup-shaped component corresponds to fitting the cup-shaped component over the annular component. The insertion of the annular component into the cup-shaped component comprises in particular screwing the annular component into the cup-shaped component or screwing the cup-shaped component onto the annular component.

The method is intended and designed in particular for assembling a medical instrument such as that described here.

The method also comprises in particular, between the step of introducing the tubular region into the annular component and the step of introducing the lever, a step of aligning the effecting device and the annular component in relation to the tubular region in such a way that the clearance in the annular component, the opening in the tubular region and the clearance in the arresting slide are in line.

The method also comprises in particular, between the steps of introducing the lever and inserting the annular component into the cup-shaped component, a step of placing an O-ring into a groove running around annularly on the outer circumference of the annular component.

The described method and its variants make it possible to produce for example a device for releasably arresting an outer shank in one or more predetermined, alternative positions in relation to an endoscope with comparatively few steps and from comparatively few components.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
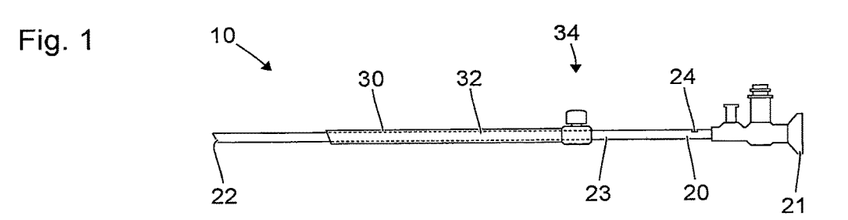
FIG. 1 shows a schematic representation of a medical instrument.

FIG. 1 shows a schematic representation of a medical instrument 10. The medical instrument 10 has two parts, which are movable in relation to one another. In the case of the example represented, these are an endoscope 20 or a similar device that can have features, properties and functions of an endoscope and an outer shank 30. The endoscope 20 has a proximal end 21—for example formed by an eyepiece—and a distal end and also a long thin shank 23. The shank 23 of the endoscope 20 has one or more clearances 24, only one of which is visible in FIG. 1.

The outer shank 30 has a substantially cylindrical cavity 32, the contours of which are indicated in FIG. 1 by dashed lines. The cross section of the cylindrical cavity 32 of the outer shank 30 and the cross section of the shank 23 of the endoscope 20 are in particular designed such that the shank 23 of the endoscope 20 is displaceable in a direction parallel to its longitudinal axis and guided with little play and little friction in the outer shank 30.

The outer shank 30 also has an arresting device 34, which in the case of the example represented is arranged at the proximal end of the outer shank 30. The arresting device 34 has an arresting slide, which is not visible in FIG. 1 and, for arresting the outer shank 30 in one or more predetermined positions on the endoscope 20, can engage in a clearance 24 or—as assumed by way of example below—alternatively in one of a number of clearances 24 on the shank 23 of the endoscope 20.

The medical instrument 10 is in particular a hysteroscope for the optical examination of the uterus. The outer shank 30 can be arrested in various positions, which are defined by the clearances 24, during the introduction of the hysteroscope and in various phases of the examination.

Figure 2:
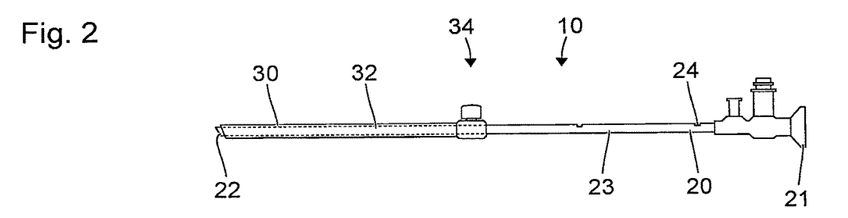
FIG. 2 shows a further schematic representation of the medical instrument from FIG. 1.

FIG. 2 shows a further schematic representation of the medical instrument 10 from FIG. 1. The type of representation corresponds to that of FIG. 1.

In FIG. 2, the outer shank 30 is shown in a position in comparison with the situation shown in FIG. 1 in which it has been displaced in the distal direction, in which the arresting slide of the arresting device 34 engages in a clearance that is not visible in the shank 23 of the endoscope 20. In FIG. 2, the clearance 24 in which the arresting slide can engage in the position of the outer shank 30 that is shown in FIG. 1 is visible in the shank 23 of the endoscope 20.

Figure 3:
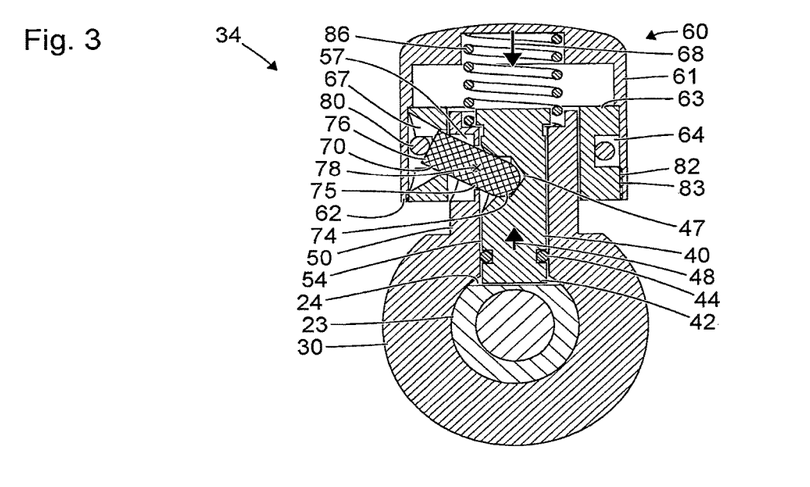
FIG. 3 shows a schematic sectional representation of an arresting device.

FIG. 3 shows a schematic representation of a section through an arresting device 34, for example through the arresting device of the medical instrument represented on the basis of FIGS. 1 and 2. The sectional plane of FIG. 3 is orthogonal to the planes of the drawing of FIGS. 1 and 2 and orthogonal to the longitudinal axis of the shank 23 of the endoscope 20. The sectional plane of the figure contains an axis of symmetry of numerous features of the arresting device 34.

As already mentioned, the arresting device 34 comprises as an effecting device an arresting slide 40 with an effecting end 42. In the case of the effecting position of the arresting slide 40 that is represented in FIG. 3, the effecting end 42 of the arresting slide 40 engages in the clearance 24 in the shank 23 of the endoscope. As a result, a predetermined position of the outer shank 30 in relation to the endoscope 20 (cf. FIGS. 1 and 2) is defined.

The arresting slide 40 also has an O-ring 44 in a groove running around near the effecting end 42. The O-ring 44 can prevent or hinder ingress into the arresting device 34 of contaminating substances and substances that put at risk the functional capability of the arresting device 34.

The arresting slide 40 also has a clearance 47. The clearance 47 in the arresting slide 40 is formed in particular by a bore in a direction orthogonal to the longitudinal axis of the arresting slide 40. The bore forming the clearance 47 has in an outer region a conical form and in the middle of the arresting slide 40 or near the axis of symmetry of the arresting slide 40 a cylindrical portion.

The arresting slide 40 is arranged in a substantially tubular region 50 on the outer shank 30. The tubular region 50 is in particular arranged at an end of the outer shank 30 with increased wall thickness. The tubular region 50 has substantially the form of a lateral surface of a circular cylinder and encloses a bore or a cavity 54, in which the arresting slide 40 is arranged. The outer cross section of the arresting slide 40 and the cross section of the cavity 54 in the tubular region 50 are designed such that the arresting slide 40 is guided in the cavity 54 with little play and little friction.

A movement of the arresting slide 40 in a first direction 48 allows the effecting end 42 of the arresting slide 40 to be lifted out from the clearance 24 in the shank 23 of the endoscope, in order to end the arrestment of the outer shank 30 in relation to the shank 23 of the endoscope. The direction 48 is orthogonal or substantially orthogonal to the longitudinal axis of the shank 23 of the endoscope.

As a departure from a purely tubular form, the tubular region 50 has an opening 57. The opening 57 is in particular created by a bore in a direction orthogonal to the first direction 48. The bore has at least in certain portions a conical form and/or at least in certain portions a rectangular longitudinal section. The cross section of the bore decreases continuously or in stages from the outside (in FIG. 3: on the left) to the inside (in FIG. 3: on the right).

The arresting device 34 also comprises a pushbutton 60 with a cup-shaped component 61. The cup-shaped component 61 has a periphery 62, which is toward the outer shank 30. Arranged in the cup-shaped component 61 is an annular component 63, which in the case of the example represented finishes flush or substantially flush with the periphery 62 of the cup-shaped component 61.

Provided on the inner side of the cup-shaped component 61, near its periphery 62, is an internal thread 82. Provided on the outer circumference of the annular component 63 is an external thread 83, corresponding to the internal thread 82. The annular component 63 is mechanically connected to the cup-shaped component 61 by a screw connection between the external thread 83 and the internal thread 82. Alternatively or in addition, the annular component 63 may be connected in an interlocking, material-bonding and/or frictionally engaging manner by a running-around welded seam, by spot welds, by an adhesive bond or by pressing or in some other way.

The annular component 63 has on its outer circumference a groove 64 running around annularly. In the annular groove 64 there lies an O-ring 80 of an elastic material. The annular component 63 also has a clearance 67. The clearance 67 is formed in particular by a bore in a direction orthogonal to the first direction 48, in which the arresting slide 40 is movable. The clearance 67 has a longitudinal section that is conical in certain portions and/or straight in certain portions. The cross section of the clearance 67 increases continuously from the inside (with respect to the annular component 63) to the outside.

One part of the pushbutton 60, specifically its region near the periphery 62, in particular the annular component 63 of the pushbutton 60, and also the tubular region 50 on the outer shank 30 and the arresting slide 40 are arranged coaxially. Apart from the clearance 47, the opening 57, the clearance 67 and the threads 82, 83, the arresting slide 40, the tubular region 50 and the pushbutton 60 are arranged rotationally symmetrically in relation to the same axis of symmetry in the sectional plane of FIG. 3.

Provided between the end of the tubular region 50 that is remote from the outer shank 30 and the inner side of the cup-shaped component 61 of the pushbutton 60 is a cavity, which on the one hand makes a movement of the pushbutton 60 in relation to the outer shank 30 possible and on the other hand contains a spring 86 between the cup-shaped component 61 of the pushbutton 60 and the tubular region 50 on the outer shank 30. The spring 86 pushes the pushbutton 60 away from the outer shank 30. The pushbutton 60 can be moved manually against the elastic force of the spring 86 in a second direction 68. The second direction 68, in which the pushbutton 60 is movable in relation to the outer shank 30, is opposite to the first direction 48, in which the arresting slide 40 is movable in relation to the outer shank 30.

The arresting device 34 also has a rocker or a lever 70 for the mechanical coupling of the pushbutton 60 with the arresting slide 40. In the case of the example represented, the lever 70 is a simple pin with a substantially circular-cylindrical form. The axis of symmetry of the lever 70 lies in the sectional plane of FIG. 3. A first end 74, which in the case of the example represented is rounded off and in particular has a hemispherical form, is arranged in the clearance 47 in the arresting slide 40. A middle region 75 of the lever 70 is arranged in the opening 57 in the tubular region 50 or passes through this opening 57. A second end 76 of the lever 70, which in the case of the example represented has a rectangular longitudinal section, is arranged in the clearance 67 in the pushbutton 60.

The clearance 47 in the arresting slide 40, the opening 57 in the tubular region 50 on the outer shank 30 and the clearance 67 in the pushbutton 60 are respectively designed such that, in the case of the situation or configuration represented in FIG. 3, the lever 70 simultaneously abuts at two points opposite one another in or near the sectional plane of FIG. 3 on the clearance 47 in the arresting slide 40 and/or simultaneously abuts at two points opposite one another in or near the sectional plane of FIG. 3 on the periphery of the opening 57 in the tubular region 50 and/or simultaneously abuts at two points opposite one another in or near the sectional plane of FIG. 3 on the periphery of the clearance 67 in the pushbutton 60. In this way, the lever 70 hinders the pushbutton 60 from moving further away from the outer shank 30 than is shown in FIG. 3. To put it another way, the position of the pushbutton 60 that is represented in FIG. 3 is the position farthest away from the outer shank 30 that is permitted by the lever 70.

Starting from the situation or configuration represented in FIG. 3, the pushbutton 60 can be moved in the second direction 68 toward the outer shank 30. In this case, the clearance 67 in the pushbutton 60 is displaced in relation to the opening 57 in the tubular region 50. This enforces a pivoting movement of the lever 70 about a pivot axis 78 orthogonally to the sectional plane of FIG. 3. The pivot axis 78 of the lever 70 is not defined by a conventional bearing. The lever 70 has neither a shaft nor a bore for a shaft nor journals nor a ridge nor a recess nor a region that is shaped as a spherical surface or is circular-cylindrical and symmetrical to the pivot axis 78 or any other conventional device for mounting. Rather, the middle region 75 of the lever 70 is merely guided through the opening 57 in the tubular region 50. As a result the pivot axis 78 of the lever 70 is also not defined as precisely as in the case of a conventional bearing. The extreme configuration represented in FIG. 3 is however definitely defined by the mentioned simultaneous abutment of the lever at two opposite points of the periphery of the opening 57 and/or at two opposite points on one of the clearances 47, 67.

If the pushbutton 60 is displaced by manual pressure from the position represented in FIG. 3 toward the outer shank 30 and the lever 70 is correspondingly pivoted about its pivot axis 78, this enforces a movement of the arresting slide 40 in the first direction 48.

Figure 4:
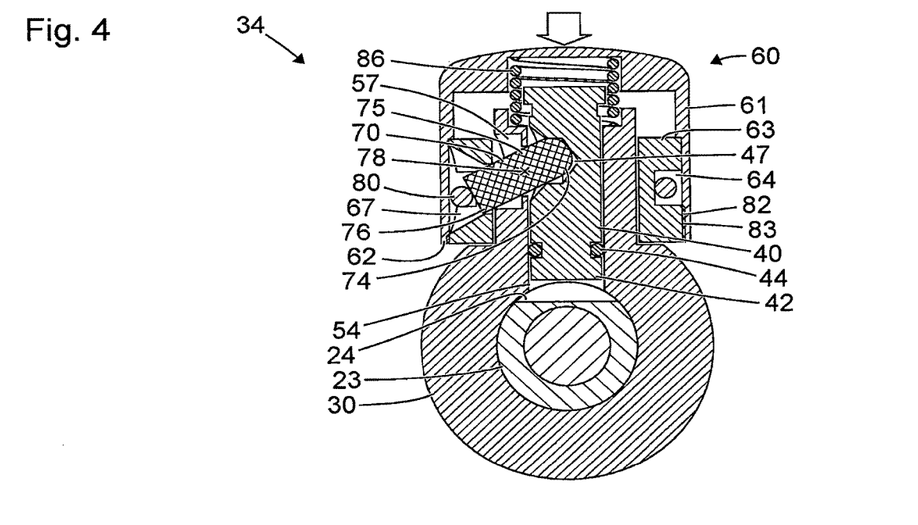
FIG. 4 shows a further schematic sectional representation of the arresting device from FIG. 3.

FIG. 4 shows a further schematic sectional representation of the arresting device 34 represented on the basis of FIG. 3. The type of representation, in particular the sectional plane, corresponds to that of FIG. 3.

FIG. 4 shows a situation or configuration that differs from that represented on the basis of FIG. 3 in that, by manual pressure on the pushbutton 60—indicated by a wide arrow—the pushbutton 60 is displaced toward the outer shank 30. In particular, FIG. 4 shows an extreme position of the pushbutton 60 opposite from the position shown in FIG. 3. In the case of the extreme position of the pushbutton 60 that is shown in FIG. 4, the pushbutton 60, in particular its periphery 62 and the annular component 63, abuts on a corresponding surface on the outer shank 30. Alternatively or in addition, the lever simultaneously abuts at two points opposite one another on the clearance 47 in the arresting slide 40 and/or simultaneously abuts at two points opposite one another on the periphery of the opening 57 in the tubular region 50 and/or simultaneously abuts at two points opposite one another on the clearance 67 in the pushbutton 60.

As already mentioned, the displacement of the pushbutton 60 from the position shown in FIG. 3 to the position shown in FIG. 4 enforces a pivoting movement of the lever 70 about its pivot axis 78 orthogonally to the planes of the drawing of FIGS. 3 and 4. The pivoting movement of the lever 70 in turn enforces a movement of the arresting slide 40 in the direction opposite to the movement of the pushbutton 60, specifically in the first direction 48, indicated in FIG. 3 by an arrow, in relation to the outer shank 30. The lever 70 consequently couples the movement of the pushbutton 60 with an opposite movement of the arresting slide 40. This coupling is not as definite in every position of the pushbutton 60 as it would be in the case of a conventional mounting of the lever 70. At least in a region between the extreme positions shown in FIGS. 3 and 4, the lever 70 has mechanical play in the opening 57 in the tubular region 50 of the outer shank 30. However, the coupling of the movement of the pushbutton 60 and the arresting slide 40 that is brought about by the lever 70 is definite, in particular in the extreme positions shown in FIGS. 3 and 4. This may be helped by the O-ring 80, which acts on the second end 76 of the lever 70 and thereby presses the first end 74 of the lever 70 at all times into the clearance 47 in the arresting slide 40.

Since, in a situation or configuration between the extreme positions represented in FIGS. 3 and 4, the O-ring 80 has the greatest elastic deformation, and consequently the greatest potential energy, the O-ring 80 can positively influence the tactile sensation when there is manual pressure on the pushbutton 60. In particular, the spring 86 and the O-ring 80 can together have the effect that the force required for moving the pushbutton 60 initially increases distinctly at the beginning of a movement from the position shown in FIG. 3 to the position shown in FIG. 4 and increases to a lesser extent, or even decreases again slightly, toward the end of the movement.

In the case of the situation or configuration shown in FIG. 4, the arresting slide 40 has been lifted completely out from the clearance 24 in the shank 33 of the endoscope. For this reason, in the situation or configuration shown in FIG. 4, the outer shank 30 can be displaced in relation to the shank 23 (cf. FIGS. 1 and 2).

Figure 5:
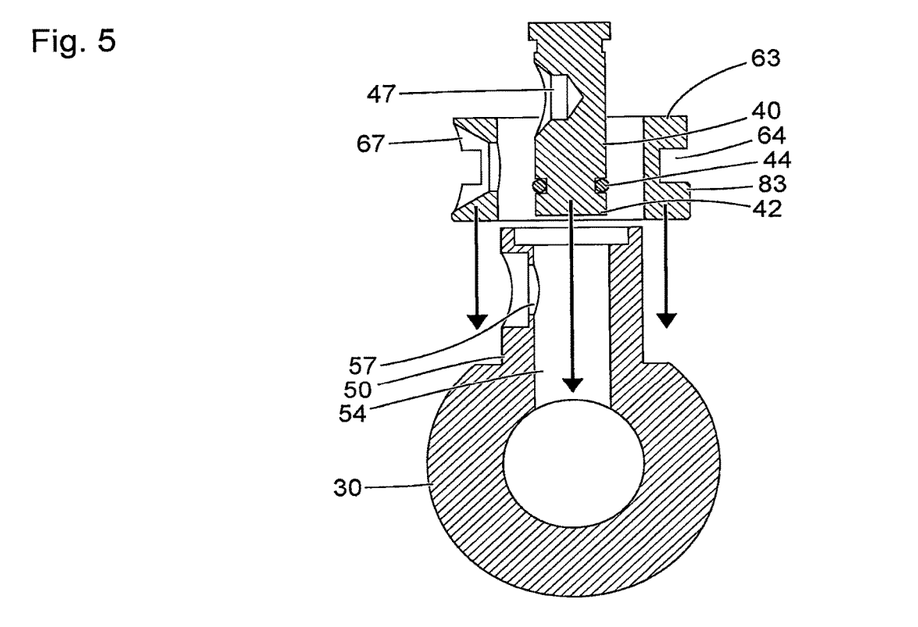
FIG. 5 shows a schematic sectional representation of component parts of the arresting device from FIGS. 3 and 4.

FIG. 5 shows a schematic representation of a section through parts of the arresting device represented on the basis of FIGS. 3 and 4. The type of representation, in particular the sectional plane, corresponds to that of FIGS. 3 and 4.

In FIG. 5, a situation during the assembly of the medical instrument or at least the arresting device is shown. In particular, the arresting slide 40 is shown in a position and an orientation in relation to the tubular portion 50 on the outer shank 30 from which it can be inserted into the cavity 54 in the tubular region 50 directly by a purely straight translational movement (indicated by the middle, longer arrow).

The annular component 63 is shown in a position and an orientation from which it can be fitted over the tubular region 50 on the outer shank 30 directly by means of a straight translational movement (indicated in FIG. 5 by the two outer, shorter arrows). This movement corresponds to an introduction of the tubular region 50 on the outer shank 30 into the annular component 63.

Figure 6:
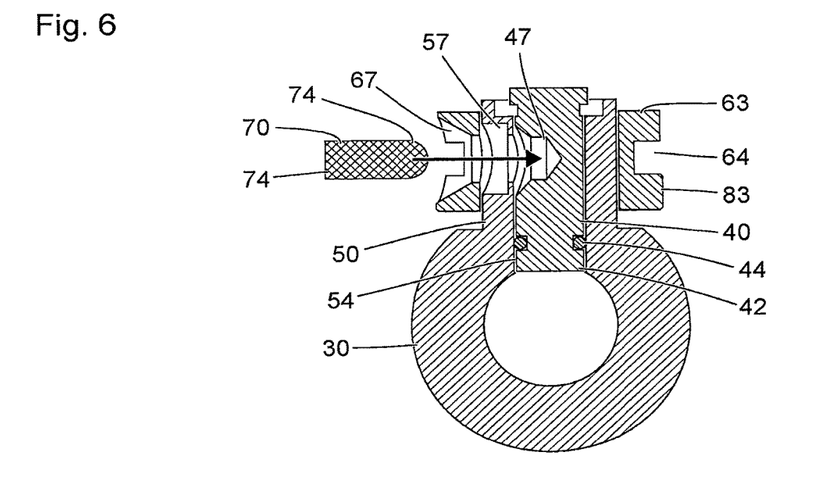
FIG. 6 shows a further schematic sectional representation of component parts of the arresting device from FIGS. 3 to 5.

FIG. 6 shows a further schematic sectional representation of parts of the arresting device represented on the basis of FIGS. 3 and 4 during assembly. The type of representation, in particular the sectional plane, corresponds to that of FIGS. 3 to 5.

In FIG. 6, a situation or configuration that follows that shown in FIG. 5 during assembly is shown. Both the arresting slide 40 and the annular component 63 are aligned in relation to the tubular region 50 on the outer shank 30 such that the clearance 47 in the arresting slide 40, the opening 57 in the tubular region 50 on the outer shank 30 and the clearance 67 in the annular component 63 are in line. In this aligned situation, the lever 70 can be inserted by a straight translational movement (indicated in FIG. 6 by an arrow). This is made possible in particular by the clearance 67 being formed by a through-bore in the annular component 63, which only thereafter is closed by the cup-shaped component 61 (cf. FIGS. 3 and 4) toward the outside, but is still open in the case of the situation represented in FIG. 6.

Figure 7:
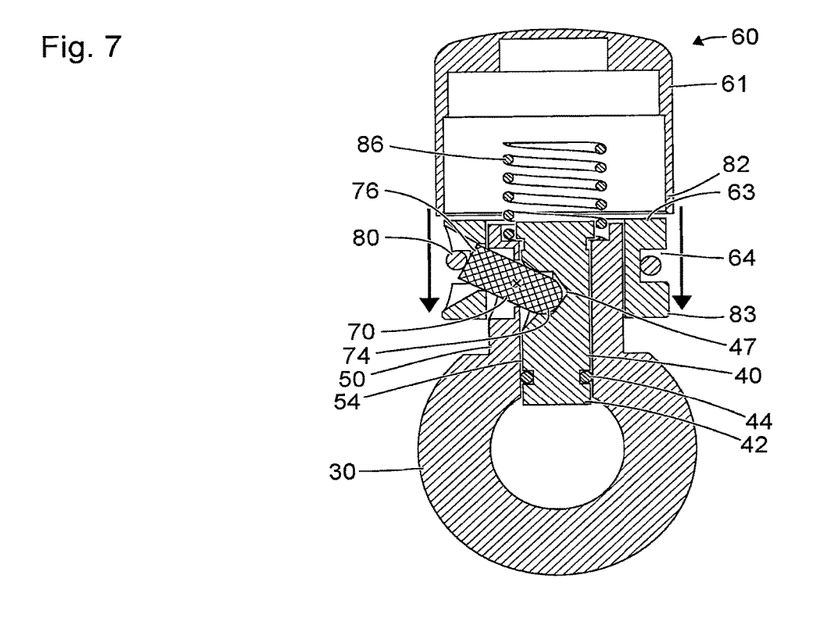
FIG. 7 shows a further schematic sectional representation of the arresting device from FIGS. 3 to 6.

FIG. 7 shows a further schematic sectional representation of all parts of the arresting device represented on the basis of FIGS. 3 and 4. The type of representation, in particular the sectional plane, corresponds to that of FIGS. 3 to 6.

The situation or configuration shown in FIG. 7 follows after that shown in FIG. 6 during assembly. The O-ring 80 has been placed into the groove 64 running around the outside of the annular component 63, abuts on the second end 76 of the lever 70 and presses the first end 74 of the lever 70 into the clearance 47 in the arresting slide 40. The spring 86, formed as a helical spring, has been fitted on the tubular region 50 on the outer shank 30.

The cup-shaped component 61 is represented in FIG. 7 in a position and orientation from which it can be fitted over the annular component 63 by a straight translational movement (indicated in FIG. 7 by two arrows). Toward the end of this translational movement, this must be accompanied by a rotation of the cup component 61 about its axis of symmetry, in order to connect the internal thread 82 on the cup-shaped component 61 to the external thread 83 on the annular component 63. Alternatively or in addition to the screwing, the cup-shaped component 61 and the annular component 63 may be connected by welding, soldering or adhesive bonding or in some other interlocking, material-bonding or frictionally engaging manner.

Figure 8:
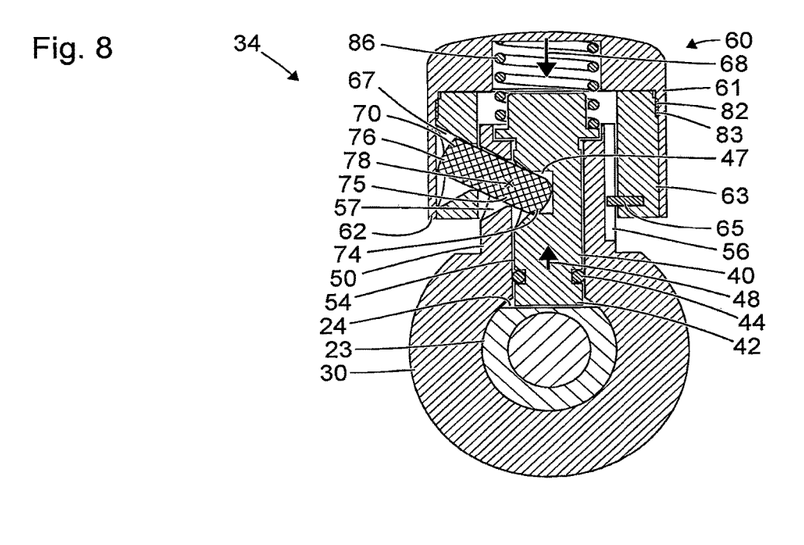
FIG. 8 shows a schematic sectional representation of a further arresting device.

FIG. 8 shows a schematic sectional representation of an alternative formation of an arresting device 34, which can for example be used for the medical instrument 10 represented on the basis of FIGS. 1 and 2. The type of representation, in particular the sectional plane, corresponds to that of FIGS. 3 to 7.

The arresting device 34 shown in FIG. 8 resembles in some features, properties and functions the arresting device represented on the basis of FIGS. 3 and 4 and can be assembled by means of method steps that resemble those represented on the basis of FIGS. 5 to 7. There follows a description of features, properties and functions by which the arresting device 34 shown in FIG. 8 differs from that represented on the basis of FIGS. 3 and 4. The features and properties in which the arresting device 34 shown in FIG. 8 differs from the arresting device represented on the basis of FIGS. 3 and 4 can be combined individually with the features and properties of the arresting device represented on the basis of FIGS. 3 and 4.

One difference between the arresting device 34 shown in FIG. 8 and the arresting device represented on the basis of FIGS. 3 and 4 is that no O-ring is provided to push the lever 70 at all times fully into the clearance 47 in the arresting slide 40. Instead, the lever 70 has a greater length and curved surfaces at the ends 74, 76. The surfaces at the ends 74, 76 of the lever 70 are in particular segments of spherical surfaces of which the center points coincide. For example, the surfaces at the ends 74, 76 of the lever 70 are segments of a spherical surface or segments of two spherical surfaces of different radii of which the center points coincide and lie for example on the pivot axis 78 of the lever 70. Alternatively, the surfaces at the ends 74, 76 of the lever 70 may be segments of surfaces of circular cylinders of which the cylinder axes coincide. In particular, the cylinder axes coincide with the pivot axis 78 of the lever 70.

This formation of the surfaces at the ends 74, 76 of the lever 70 allows the lever 70 to be guided within an angular range, which depends on the diameter of the lever 70, with little play and little friction between the in this case planar end wall of the clearance 47 in the arresting slide 40 and the inner surface of the cup-shaped component 61.

A further difference is that, in the case of the arresting device 34 shown in FIG. 8, the internal thread 82 on the cup-shaped component 61 and the corresponding external thread 83 on the annular component 63 are arranged differently, specifically near the periphery of the annular component 63 that is remote from the periphery 62 of the cup-shaped component 61. The O-ring 80 (in the case of a formation of the lever 70 corresponding to the representation on the basis of FIGS. 3 and 4) or the lever 70 itself (in the case of its formation corresponding to the representation on the basis of FIG. 8) therefore does not come into contact with the internal thread 82 on the cup-shaped component 61 even during assembly.

A further difference is that, in the case of the arresting device 34 shown in FIG. 8, the opening 57 in the tubular region 50 on the outer shank 30 is predominantly conically designed. Not only the clearance 47 in the arresting slide 40 but also the opening 57 in the tubular region 50 on the outer shank 30 and also the clearance 67 in the pushbutton 60 may be respectively designed to be conical in certain portions, largely conical or completely conical or designed to be rectangular in certain portions in the longitudinal section or may have cross sections that vary in the form of stages.

A formation such that the annular region of minimum cross section is designed to be as narrow as possible (as also applies to the opening 57 in the tubular region 50 on the outer shank 30 and to the clearance 67 in the pushbutton 60 in the case of all the exemplary embodiments described here) is advantageous because, with a given maximum pivoting angle of the lever 70, the play of the lever in positions between the extreme positions shown in FIGS. 3, 4 and 8 is minimized. To help to achieve the same aim, the cylindrical part of the lever, dominating the form of the lever 70 between its ends 74, 76, enters the cylindrical portion of the clearance 47 in the arresting slide 40 as little as possible.

A further difference is that the arresting device shown in FIG. 8 has on the annular component 63 a pin 65 that protrudes inwardly or into the spatial region enclosed by the annular component 63. The pin 65 on the annular component 63 engages in a corresponding groove 56 in the tubular region 50 on the outer shank 30. The groove 56 is straight and parallel to the second direction 68, in which the pushbutton 60 is movable from its position shown in FIG. 8. The pin 65 on the annular component 63 and the groove 56 in the tubular region 50 on the outer shank 30 are respectively intersected by the sectional plane of FIG. 8, but may alternatively be provided at other positions. The groove 56 is of such a length that the annular component 63 can be fitted over the tubular region 50, as represented on the basis of FIG. 5.

The engagement of the pin 65 on the annular component 63 in the groove 56 in the tubular region 50 on the outer shank 30 prevents rotation of the annular component 63, and consequently also of the entire pushbutton 60, in relation to the tubular region 50 on the outer shank 30. Such a rotation can admittedly also be prevented by the lever 70. The engagement of the pin 65 on the annular component 63 in the groove 56 on the tubular region 50 makes more precise guidance possible however, and relieves the lever 70 of this secondary task.

A further difference is that, in the case of the arresting device 34 shown in FIG. 8, the spring 86 is not arranged between the tubular region 50 on the outer shank 30 and the pushbutton 60, but between the arresting slide 40 and the pushbutton 60. Furthermore, the end of the arresting slide 40 that is toward the spring 86 and the cup-shaped component 61 are designed such that the spring 86 is at all times guided virtually over its entire length at least either by the arresting slide 40 or by the cup-shaped component 61.

Figure 9:
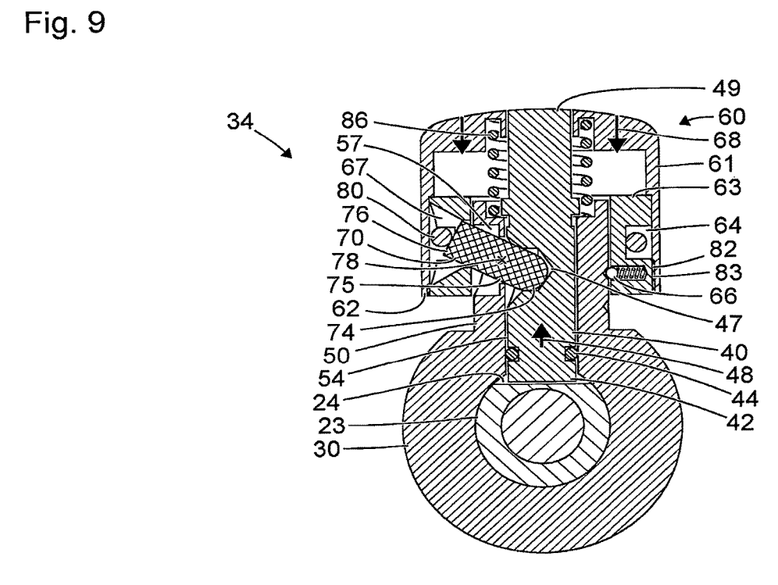
FIG. 9 shows a schematic sectional representation of a further arresting device.

FIG. 9 shows a schematic sectional representation of an alternative formation of an arresting device 34, which can be used for example for the medical instrument 10 represented on the basis of FIGS. 1 and 2. The type of representation, in particular the sectional plane, corresponds to that of FIGS. 3 to 8.

The arresting device 34 shown in FIG. 9 resembles in some features, properties and functions the arresting devices represented on the basis of FIGS. 3 to 8 and can be assembled by means of method steps that resemble those represented on the basis of FIGS. 5 to 7. There follows a description of features, properties and functions by which the arresting device 34 shown in FIG. 9 differs from that represented on the basis of FIGS. 3 to 8. The features and properties in which the arresting device 34 shown in FIG. 9 differs from the arresting devices represented on the basis of FIGS. 3 to 8 can be combined individually with the features and properties of the arresting devices represented on the basis of FIGS. 3 to 8.

One difference between the arresting device 34 shown in FIG. 9 and the arresting device represented on the basis of FIGS. 3 to 8 is that the cup-shaped component 61 of the pushbutton 60 has an opening in which one end 49 of the arresting slide 40 is arranged and is visible from the outside. The end 49 of the arresting slide 40 that is visible in the opening in the cup-shaped component 61 is the end that is opposite from the effecting end 42 of the arresting slide 40, i.e. is remote from it.

In the case of the situation or configuration shown in FIG. 9, the arresting slide 40 is located in its intended effecting position, which is defined in an interlocking manner. The effecting end 42 of the arresting slide 40 engages in the clearance 24 in the endoscope. In this effecting position of the arresting slide, the visible end 49 of the arresting slide is flush with the surrounding region of the cup-shaped component 61. The effecting position of the arresting slide can be quickly and clearly perceived from this, both in visual and tactile respects.

The arresting device 34 shown in FIG. 9 also differs from the arresting devices represented on the basis of FIGS. 3 to 8 in that a latching device 66 is provided between the pushbutton 60 and the tubular region 50 on the outer shank 30. This latching device 66 is indicated by way of example by a ball, which is pressed by a spring into one of two clearances on the tubular region 50 on the outer shank 30.

The latching device 66 has the effect that the arresting slide 40 and the pushbutton 60 stay in their positions shown in FIG. 9 even whenever small forces act on them. In order to deflect the pushbutton 60, and consequently also the arresting slide 40, out of their positions shown in FIG. 9, the force of the spring 86 and the latching force of the latching device 66 must be overcome.

Starting from the situation or configuration represented in FIG. 9, the pushbutton 60 can be moved in the second direction 68 toward the outer shank 30. As already represented on the basis of FIGS. 3 and 4, a movement of the pushbutton 60 in the second direction 68 is accompanied by a pivoting movement of the lever 70 and a movement of the arresting slide 40 in the first direction 48.

Figure 10:
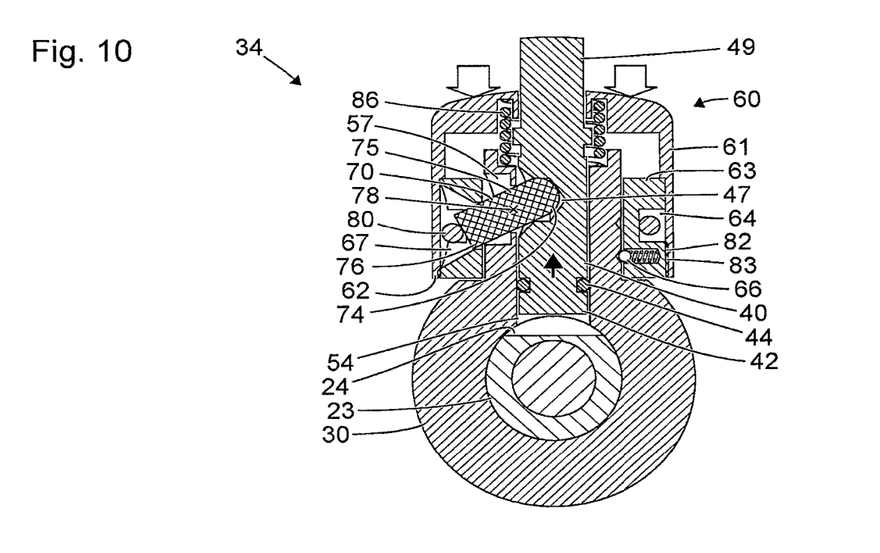
FIG. 10 shows a further schematic sectional representation of the arresting device from FIG. 9.

FIG. 10 shows a further schematic sectional representation of the arresting device 34 represented on the basis of FIG. 9. The type of representation, in particular the sectional plane, corresponds to that of FIG. 9.

FIG. 10 shows a situation or configuration that differs from that represented on the basis of FIG. 9 in that, by manual pressure on the pushbutton 60—indicated by wide arrows—the pushbutton 60 is displaced toward the outer shank 30. In particular, FIG. 10 shows an extreme position of the pushbutton 60 opposite from the position shown in FIG. 9. In the case of the extreme position of the pushbutton 60 that is shown in FIG. 10, the pushbutton 60, in particular its periphery 62 and the annular component 63, abuts on a corresponding surface on the outer shank 30. Alternatively or in addition, the lever simultaneously abuts at two points opposite one another on the clearance 47 in the arresting slide 40 and/or simultaneously abuts at two points opposite one another on the periphery of the opening 57 in the tubular region 50 and/or simultaneously abuts at two points opposite one another on the clearance 67 in the pushbutton 60.

As already represented on the basis of FIGS. 3 and 4, the displacement of the pushbutton 60 from the position shown in FIG. 9 to the position shown in FIG. 10 enforces a pivoting movement of the lever 70 about its pivot axis 78 orthogonally to the planes of the drawing of FIGS. 9 and 10 and a movement of the arresting slide 40 in the first direction 48 opposite to the movement of the pushbutton 60.

Alternatively and as a departure from the representation on the basis of FIGS. 9 and 10, the spring 86 may be omitted. In this case, the arresting slide 40 can be moved into its effecting position shown in FIG. 9 by manual pressure on the visible end 49, and the arresting device 40 can be moved out of its effecting position into the position shown in FIG. 10 by manual pressure on the pushbutton 60.

Furthermore, as a departure from the representation in FIGS. 9 and 10, the latching device 66 may only have a depression at the tubular region 50 on the outer shank 30. If the arresting device 34 has the spring 86, the latching device 66 has in particular only the depression that fixes the pushbutton 60 in the position shown in FIG. 10.

Alternatively and as a departure from the representation on the basis of FIGS. 9 and 10, the latching device 66 may be omitted entirely.

Figure 11:
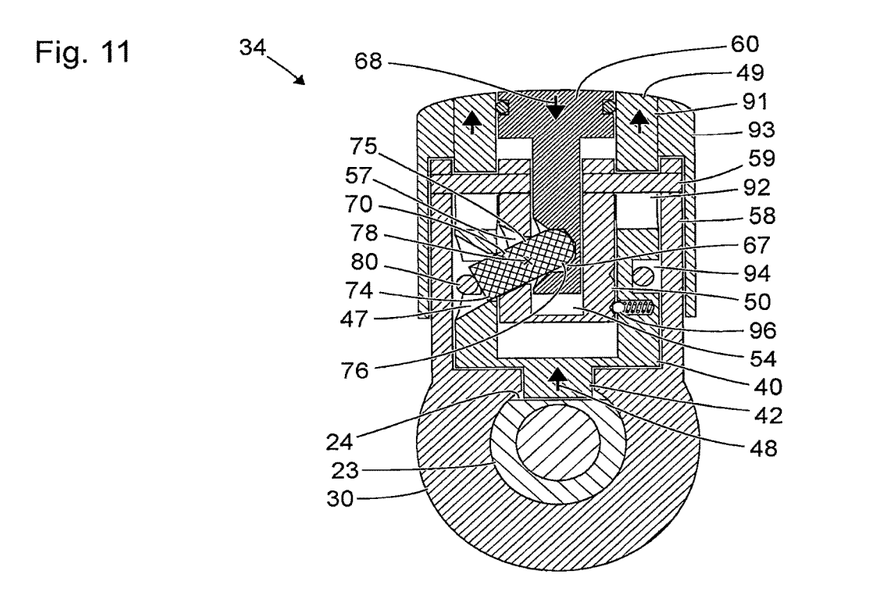
FIG. 11 shows a schematic sectional representation of a further arresting device.

FIG. 11 shows a schematic sectional representation of an alternative formation of an arresting device 34, which can be used for example for the medical instrument 10 represented on the basis of FIGS. 1 and 2. The type of representation, in particular the sectional plane, corresponds to that of FIGS. 3 to 10.

The arresting device 34 shown in FIG. 11 resembles in some features, properties and functions the arresting devices represented on the basis of FIGS. 3 to 10 and can be assembled by means of method steps that resemble those represented on the basis of FIGS. 5 to 7. There follows a description of features, properties and functions by which the arresting device 34 shown in FIG. 11 differs from that represented on the basis of FIGS. 3 to 10. The features and properties in which the arresting device 34 shown in FIG. 11 differs from the arresting devices represented on the basis of FIGS. 3 to 10 can be partially combined individually with the features and properties of the arresting devices represented on the basis of FIGS. 3 to 10.

In a way similar to in the case of the arresting device represented on the basis of FIGS. 9 and 10, also in the case of the arresting device 34 shown in FIG. 11 the arresting slide 40 has a visible end 49. In the case of both examples, the visible end 49 of the arresting slide 40 and the pushbutton 60 are arranged concentrically. As a difference from the arresting device represented on the basis of FIGS. 9 and 10, however, in the case of the arresting device 34 shown in FIG. 11 it is not the visible end 49 of the arresting slide 40 that is surrounded by the pushbutton 60, but the pushbutton 60 that is surrounded by the visible end of the arresting slide 40.

In the case of the arresting device 34 shown in FIG. 11, the pushbutton 60 has a substantially pin-shaped form. In the case of the example represented, the visible end of the pushbutton 60 has an increased diameter.

The pushbutton 60 is partially arranged in a tubular region 50 on the outer shank 30 of the medical instrument. In the case of the example shown in FIG. 11, the tubular region 50 is closed at one end, specifically at the end remote from the visible end of the pushbutton 60 and toward the outer shank 34, therefore altogether has a cup-shaped form.

The tubular region 50 is formed by a component that is connected mechanically rigidly to a further tubular region 58 by way of a number of pins 59. The further tubular region 58 is connected directly to the outer shank 34 and may be formed integrally or monolithically with it.

The arresting slide 40 is largely formed by a substantially cup-shaped component 91. The effecting end 42 is provided at the bottom of the cup-shaped component 91. The periphery of the cup-shaped component 91 forms a part of the visible end 49 of the arresting slide 40 and encloses the pushbutton 60 annularly. A region of the cup-shaped component 91 between the bottom and the periphery that substantially has the form of a lateral surface of a circular cylinder is partially arranged in an annular gap between the tubular region 50 and the further tubular region 58 on the outer shaft 34 and has a number of slits 92. Each slit 92 extends in a direction parallel to the direction 48 in which the arresting slide 40 is movable. Each slit 32 is passed through by a pin 59, which connects the tubular region 50 within the cup-shaped component 91 mechanically rigidly to the further tubular region 58 outside the cup-shaped component 91.

The arresting slide 40 also comprises a tubular component 93, which is connected mechanically rigidly to the periphery of the cup-shaped component 91, in particular is joined by laser welding. The tubular component 93 encloses the further tubular region 58 on the outer shank 34 and, together with the periphery of the cup-shaped component 91, forms the visible end 49 of the arresting slide 40.

In a way similar to in the case of the arresting devices represented on the basis of FIGS. 3 to 10, a lever 70 passes through an opening 57 in the tubular region 50 on the outer shank 30. The opening 57 defines in an interlocking manner a pivot axis 78 in a middle region 75 of the lever 70, about which the lever 70 is pivotable. A first end 74 of the lever 70 engages in an opening 47 in the cup-shaped component 91 of the arresting slide 40. A second end 76 of the lever 70 engages in a clearance 67 in the pushbutton 60.

An O-ring 80 of an elastic material is arranged in a groove 94 in the cup-shaped component 91 of the arresting slide 40. The groove 94 intersects the opening 47 in the cup-shaped component 91. In the region of the opening 47, the O-ring 80 abuts on the first end 74 of the lever 70. The O-ring 80 exerts a force on the lever 70, which presses the second end 76 of the latter into the clearance 67 in the pushbutton 60.

Provided between the cup-shaped component 91 of the arresting slide 40 and the tubular region 50 on the outer shank 34 is a latching device 96. The latching device defines in relation to the tubular region 50 two positions of the arresting slide 40, in which the arresting slide 40 latches. The latching device 96 is represented by way of example as a spring-loaded ball, which alternatively engages in one of two small clearances at the tubular region 50 on the outer shank 34.

In a way similar to in the case of the arresting devices represented on the basis of FIGS. 3 to 10—a spring which pushes the arresting slide 40 into the effecting position shown in FIG. 11 may be provided alternatively or in addition to the latching device 96.

In the case of the arresting device 34 shown in FIG. 11, the visible ends of the arresting slide 40 and of the pushbutton 60 are arranged flush or in line when the arresting slide 40 assumes its effecting position shown in FIG. 11. For this reason, it is quickly and clearly perceptible in both visual and tactile respects when the arresting slide 40 assumes its effecting position.

Figure 12:
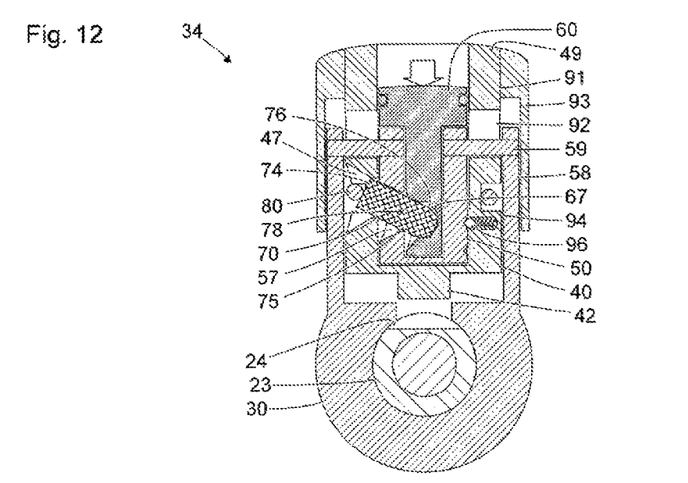
FIG. 12 shows a further schematic sectional representation of the arresting device from FIG. 11.

FIG. 12 shows a further schematic sectional representation of the arresting device 34 represented on the basis of FIG. 11. The type of representation, in particular the sectional plane, corresponds to that of FIG. 11.

FIG. 12 shows a situation or configuration that differs from that represented on the basis of FIG. 11 in that, by manual pressure on the pushbutton 60—indicated by a wide arrow—the pushbutton 60 is displaced toward the outer shank 30. In particular, FIG. 12 shows an extreme position of the pushbutton 60 that is defined in an interlocking manner and opposite from the position shown in FIG. 11.

As already represented on the basis of FIGS. 3, 4, 9 and 10, the displacement of the pushbutton 60 from the position shown in FIG. 11 to the position shown in FIG. 12 enforces a pivoting movement of the lever 70 about its pivot axis 78 orthogonally to the planes of the drawing of FIGS. 11 and 12 and a movement of the arresting slide 40 in the first direction 48 opposite to the movement of the pushbutton 60.

For moving the arresting slide 40 out of the effecting position shown in FIG. 11 into the position shown in FIG. 12, the pushbutton 60 must be moved into the position shown in FIG. 12, lowered with respect to the visible end 49 of the arresting slide 40. This largely rules out unintentional actuation of the pushbutton 60.

Figure 13:
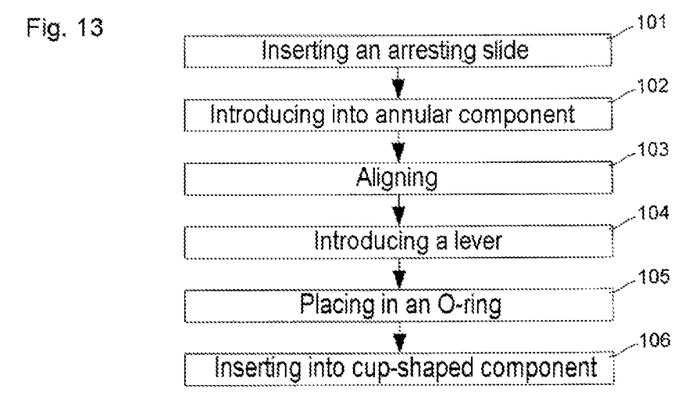
FIG. 13 shows a schematic flow diagram of a method for assembling a medical instrument.

FIG. 13 shows a schematic flow diagram of a method for assembling a medical instrument, in particular an arresting device on a medical instrument. The method can also be applied to medical instruments and arresting devices that have features, properties and functions that deviate from those represented on the basis of FIGS. 1 to 12. Nevertheless, reference signs from FIGS. 1 to 12 are used below to simplify understanding.

In the case of a first step 101, an arresting slide 40 or some other effecting device is inserted into a tubular region 50, in particular into a cavity 54 in a tubular region 50 of the medical instrument 10. In the case of a second step 102, the tubular region 50 is introduced into an annular component 63 or the annular component 63 is fitted over the tubular region 50. The first step 101 and the second step 102 may be performed in the sequence represented or at the same time or in the reverse sequence.

In the case of a third step 103, the effecting device 40 and the annular component 63 are aligned in relation to the tubular region 50 such that a clearance 67 in the annular component 63, an opening 57 in the tubular region 50 and a clearance 47 in the arresting slide 40 are in line. The third step 103 may be performed in two sub-steps already at the same time as the first step 101 and/or at the same time as the second step 102.

In the case of a fourth step 104, a lever 70 is introduced into the clearance 67 in the annular component 63, into the opening 57 in the tubular region 50 and into the clearance 47 in the effecting device 40.

In the case of an optional fifth step 105, an O-ring 80 is inserted into a groove 64 running around annularly on the outer circumference of the annular component 63.

In the case of a sixth step 106, the annular component 63 is inserted into a cup-shaped component 61 or the cup-shaped component 61 is fitted over the annular component 63. The sixth step 106 comprises in particular a permanent mechanical connection of the annular component 63 to the cup-shaped component 61 by screwing and/or in some other interlocking, material-bonding and/or frictionally engaging manner. The sixth step 106 is accompanied in particular by closing of a through-bore, forming the clearance 67 in the annular component 63, at its radially outer end by the cup-shaped component 63. In this way, the lever 70 is enclosed in the clearance 47 in the effecting device 40, in the opening 57 in the tubular region 50 and in the clearance 67 in the annular component 63.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A medical instrument, comprising:
    an effecting device, which is movable in a first direction from a first effecting position into a second effecting position;
    a pushbutton, which is movable manually in a second direction from a first button position into a second button position; and
    a lever, which is pivotable about a pivot axis, the second direction being different from the first direction, the lever mechanically coupling the pushbutton and the effecting device in such a way that a movement of the pushbutton in the second direction is accompanied by a movement of the effecting device in the first direction; the lever not having an area that is rotationally symmetrical to the pivot axis in the region of its pivot axis.

2. The medical instrument according to claim 1, wherein a middle region of the lever protrudes through an opening in a wall between the pushbutton and the effecting device, the middle region of the lever is mechanically guided through the opening in the wall such that the lever is pivotable about the pivot axis, but is not significantly displaceable in the first direction or the second direction.

3. The medical instrument according to claim 1, wherein the wall has a reduced thickness in the vicinity of the opening.

4. The medical instrument according to claim 1, wherein the lever has a first end, which engages in a clearance in the effecting device, the lever has a second end, which engages in a clearance in the pushbutton.

5. The medical instrument according to claim 1, further comprising:
    an O-ring of an elastic material,
    wherein either the O-ring abutting on the second end of the lever and pushing the first end of the lever into the clearance in the effecting device or the O-ring abutting on the first end of the lever and pushing the second end of the lever into the clearance in the pushbutton.

6. The medical instrument according to claim 5, wherein the annular component has a groove that runs around annularly on its outer circumference and wherein the O-ring is placed.

7. The medical instrument according to claim 1, wherein the effecting device is an arresting slide or is mechanically coupled with an arresting slide, the arresting slide is intended for the interlocking retention of a component part of the mechanical instrument in a predetermined position.

8. The medical instrument according to claim 1, wherein the wall surrounds the effecting device annularly, a region of the pushbutton surrounds the wall annularly.

9. The medical instrument according to claim 1, wherein the effecting device is guided through the wall in an interlocking manner, the pushbutton is guided through the wall in an interlocking manner.

10. The medical instrument according to claim 1, wherein the pushbutton comprises a cup-shaped component and an annular component inserted into a cavity of the cup-shaped component, the clearance in the pushbutton is formed in the annular component.

11. The medical instrument according to claim 10, wherein the clearance in the pushbutton is formed by a window-shaped opening or a through-bore in the annular component.

12. The medical instrument according to claim 1, wherein interlocking between the lever and the pushbutton and interlocking between the lever and the opening in the wall prevent the pushbutton from being pulled off from the medical instrument.

13. The medical instrument according to claim 1, wherein the medical instrument is a hysteroscope with an endoscope and an outer shank, the endoscope is displaceable in relation to the outer shank in an axial direction, the effecting device is an arresting device, the effecting device is intended and designed to engage in a clearance on the endoscope in the first effecting position, in order in this way to arrest the endoscope in a predetermined position in relation to the outer shank.

* * * * *